United States Patent [19]

Coursen

[11] 4,362,747
[45] Dec. 7, 1982

[54] COSMETIC CREAM PACK FORMULATION

[75] Inventor: Lawrence J. Coursen, Indianapolis, Ind.

[73] Assignee: Eli Lilly and Company, Indianapolis, Ind.

[21] Appl. No.: 289,654

[22] Filed: Aug. 3, 1981

[51] Int. Cl.³ .............................................. A61K 47/00
[52] U.S. Cl. ..................................... 424/358; 424/365
[58] Field of Search .......................................... 424/358

[56] References Cited

U.S. PATENT DOCUMENTS 3,818,105 6/1974 Coopersmith ....................... 424/358
4,272,544 6/1981 Cella et al. ........................... 424/273

FOREIGN PATENT DOCUMENTS 49-19046 2/1974 Japan .................................... 424/358

OTHER PUBLICATIONS

Elizabeth Arden, Product Line—SUN CARE ®—Self Tanning Cream.
Elizabeth Arden, Product Line—CABRIOLE ®—Body Lotion.
Elizabeth Arden, Product Line—CHLOE ®—Satine Body Lotion.
Formulary of Cosmetic Preparations, 1977 Ash, pp. 423 to 425, 253 to 257 & 293.

Primary Examiner—Dale R. Ore
Attorney, Agent, or Firm—Karen B. O'Connor; Arthur R. Whale

[57] ABSTRACT

A novel cosmetic skin cream pack formulation is described which is non-irritating and non-stinging.

1 Claim, No Drawings

COSMETIC CREAM PACK FORMULATION

This invention relates to a novel cosmetic cream pack formulation, which is non-irritating and non-stinging.

The cream pack can be used in conjunction with other cosmetic formulations. For example, it can be used with four components of a sensitive-skin line. Each of the four components is a separate invention; a cleanser is claimed in application Ser. No. 289,657, filed Aug. 3, 1981; a toner is claimed in application Ser. No. 289,656, filed Aug. 3, 1981; a moisturizer is claimed in application Ser. No. 289,655, filed Aug. 3, 1981; and a cream is claimed in application Ser. No. 289,653, filed Aug. 3, 1981. A method of treating sensitive skin using the four components is claimed in application Ser. No. 289,658, filed Aug. 3, 1981.

The cream pack formulation consists essentially of, in percent by weight:

| Ingredients | Percent |
| --- | --- |
| Propylene glycol | 2.90 |
| polyoxyethylene (20) sorbitan monopalmitate | 4.00 |
| glyoxyldiureide | 0.50 |
| 85% mineral oil/15% lanolin alcohol | 5.00 |
| white beeswax | 3.00 |
| sorbitan monopalmitate | 4.00 |
| polyoxyethylene (5) C-16/18 alcohol | 6.00 |
| dimethicone copolyol | 1.00 |
| glyceryl monostearate/polyoxyethylene (100) stearate | 3.00 |
| zinc oxide | 6.00 |
| corn starch | 10.00 |
| preservative | q.s. |
| deionized water | q.s. to 100% |

One skilled in the cosmetic formulation art will appreciate that various typical preservatives can be added to the cream pack formulation in sufficient quantity. Typical preservatives include esters of p-hydroxybenzoic acid such as methyl p-hydroxybenzoate, and propyl p-hydroxybenzoate; cis-1-(3-chloroallyl)3,5,7-triaza-1-azoniaadamantane chloride; ethylenediaminetetraacetic acid (EDTA) and salts of EDTA; imidazolidinyl urea; sodium N-lauryl-$\beta$-iminodipropionate; and the like or any combination thereof. The total amount of preservative used is from about 0.3 to about 1.0 percent by weight.

In addition, color and essence can be included in the formulation as desired. Color additives would include both natural and artificial dyes, such as carotenoid derivatives, D+C or F,D+C colors, iron oxides, and the like, while essences can include any non-irritating natural and artifical oils, perfumes, and the like.

The cream pack formulation is both non-irritating and non-stinging, according to standard cosmetic test procedures. The first procedure utilized was the Lanman-Maibach Cumulative Irritation Test, which is a 21-day patch irritation procedure as described by Dr. B. M. Lanman at the Joint Conference on Cosmetic Sciences, April 21-23, 1968 in Washington, D.C. and as further modified in the procedure of Phillips, L., Steinberg, M., Maibach, H., and Akers, W., *Toxicology and Applied Pharmacology* 21, 369-382 (1972). The results of this test showed the cream pack formulation to be non-irritating. The non-stinging properties of the formulation were established by the Lactic Acid Sting Test as described in P. J. Frosch and A. M. Kligman: "A Method for Appraising the Stinging Capacity of Topically Applied Substances" *Journal of the Society of Cosmetic Chemists* 28, 197-209, May 1977.

In general, the individual ingredients used in the formulation should be of a quality or purity (such as U.S.P. or N.F.) suitable for cosmetic use.

The formulation is prepared by mixing the ingredients according to conventional cosmetic methods and the preparation of the formulation is described in the following example. The example is illustrative of the formulation, but is not to be construed as limiting the invention.

EXAMPLE

Cream Pack

Formulation:

| Phase | Ingredient | Percent by weight |
| --- | --- | --- |
| A | deionized water | 53.00 |
|  | propylene glycol | 2.90 |
|  | methylparaben (methyl p-hydroxybenzoate) | 0.25 |
|  | Polysorbate 40 (I.C.I. United States, polyoxyethylene (20) sorbitan monopalmitate | 4.00 |
|  | Allantoin (Sutton and Schuylkill, glyoxyldiureide) | 0.50 |
| B | Amerchol L-101 (Amerchol, 85% mineral oil/15% lanolin alcohol) | 5.00 |
|  | white beeswax | 3.00 |
|  | propylparaben (propyl p-hydroxybenzoate) | 0.15 |
|  | sorbitan monopalmitate (ICI, United States) | 4.00 |
|  | Polawax (Croda, polyoxyethylene (5) C-16/18 alcohol) | 6.00 |
|  | Silicone L-7001 (Union Carbide, dimethicone copolyol) | 1.00 |
|  | GMS/PEG-100 stearate (I.C.I. United States, glyceryl monostearate/polyoxyethylene (100) stearate | 3.00 |
| C | zinc oxide | 6.00 |
| D | corn starch | 10.00 |
| E | Dowicil 200 (Dow Chemical, cis-1-(3-chloroallyl)-3,5,7-triaza-1-azoniaadamantane chloride) | 0.20 |
|  | deionized water | 1.00 |

Procedure:

The ingredients of Phase A are heated to about 75°-80° C. and mixed in a vessel equipped with a sweep mixer and a homomixer. The ingredients of Phase B are heated in a separate vessel to about 75°-80° C. and mixed until the mixture is melted and uniform. Then Phase B is added to Phase A and while mixing, Phase AB is cooled to about 60°-65° C.

Phase C is added to Phase AB with mixing by the homomixer. Phase ABC is cooled to about 55°-60° C. and Phase D is added with mixing. After Phase D is evenly dispersed, Phase E is added. Phase ABCDE is mixed with the side-sweep agitator and homomixer while cooled to about 30°-35° C.

I claim:

1. A cosmetic cream pack formulation consisting essentially of, in percent by weight:

| Ingredients | Percent |
| --- | --- |
| Propylene glycol | 2.90 |

| Ingredients | Percent |
| --- | --- |
| polyoxyethylene (20) sorbitan monopalmitate | 4.00 |
| glyoxyldiureide | 0.50 |
| 85% mineral oil/15% lanolin alcohol | 5.00 |
| white beeswax | 3.00 |
| sorbitan monopalmitate | 4.00 |
| polyoxyethylene (5) C-16/18 alcohol | 6.00 |
| dimethicone copolyol | 1.00 |
| glyceryl monostearate/polyoxyethylene (100) stearate | 3.00 |
| zinc oxide | 6.00 |
| corn starch | 10.00 |
| preservative | q.s. |
| deionized water | q.s. to 100% |

* * * * *